United States Patent [19]

Miura et al.

[11] Patent Number: 4,755,617
[45] Date of Patent: Jul. 5, 1988

[54] PROCESS FOR THE PREPARATION OF 4'-HYDROXYBIPHENYL-4-CARBOXYL ACID

[75] Inventors: Tohru Miura; Teruyuki Nagata; Hideki Mizuta, all of Ohmuta, Japan

[73] Assignee: Mitsui Toatsu Chemicals, Incorporated, Tokyo, Japan

[21] Appl. No.: 31,709

[22] Filed: Mar. 30, 1987

[30] Foreign Application Priority Data

Apr. 4, 1986 [JP] Japan .................. 61-76684
Jul. 8, 1986 [JP] Japan .................. 61-158707
Sep. 24, 1986 [JP] Japan .................. 61-223889

[51] Int. Cl.$^4$ .............................. C07C 09/76
[52] U.S. Cl. .................... 560/059; 562/469; 562/508
[58] Field of Search .............. 562/469; 560/059

[56] References Cited

U.S. PATENT DOCUMENTS 3,957,851 5/1976 Satzinger et al. ............. 560/059
3,970,694 7/1976 Minai et al. .................. 560/059
4,537,704 8/1985 Sprecker et al. .............. 252/522

FOREIGN PATENT DOCUMENTS 0142322 5/1985 European Pat. Off. .
715545 9/1954 United Kingdom ............. 560/059
1325056 8/1973 United Kingdom ............. 562/469

OTHER PUBLICATIONS

Journal of American Chemical Society, 58, 1738 (1936).
Bulletin of the Chemical Society of Japan, 30, 508–13 (1957).
Method der organischen Chemie, vol. 6/1c, No. 2, (1976), p. 1028.

Primary Examiner—Paul J. Killos
Attorney, Agent, or Firm—Fisher, Christen & Sabol

[57] ABSTRACT

A process for the preparation of 4'-hydroxybiphenyl-4-carboxylic acid by reacting a cyclohexanone-4-carboxylic acid compound with phenol in the presence of an acid catalyst, and then subjecting the resulting 4,4-bis(4-hydroxyphenyl)cyclohexanecarboxylic acid compound to decomposition and dehydrogenation reactions in the presence of a base and a dehydrogenation catalyst. The aforesaid cyclohexanone-4-carboxylic acid compound is obtained by catalytically hydrogenating a 4-hydroxybenzoic acid compound in a secondary alcohol or tertiary alcohol solvent, and the reaction mixture thus obtained is directly used for the reaction with phenol.

9 Claims, No Drawings

PROCESS FOR THE PREPARATION OF 4'-HYDROXYBIPHENYL-4-CARBOXYL ACID

BACKGROUND OF THE INVENTION a. Field of the Invention

This invention relates to a novel process for the preparation of 4'-hydroxybiphenyl-4-carboxylic acid from cyclohexanone-4-carboxylic acid compounds.

b. Description of the Prior Art

4'-Hydroxybiphenyl-4-carboxylic acid is very important as a raw material for the synthesis of polymers and as an intermediate for the synthesis of liquid crystals. Only a few processes for the preparation of this compound have been proposed, and the following three processes are found in the literature.

(a) A process which comprises converting p-phenylphenol into p-methoxybiphenyl, synthesizing 4-methoxy4'-acetobiphenyl therefrom by the Friedel-Crafts reaction, oxidizing it to 4-methoxy-4'-carboxybiphenyl, and then treating the latter with hydrobromic acid to obtain the desired compound [Journal of American Chemical Society, 58, 1738 (1936)].

(b) A process which comprises reacting p-iodobenzoic acid methyl ester with p-iodoanisole to form 4methoxy-4'-carboxybiphenyl, and then treating it in the same manner as described in the process (a) to obtain the desired compound [Bulletin of the Chemical Society of Japan, 30, 508–13 (1957)].

(c) A process which comprises diazotizing 4'-aminobiphenyl-4-carboxylic acid and hydrolyzing the resulting product to obtain the desired compound [French Patent No. 735,846].

As to the preparation of cyclohexanone-4-carboxylic acid and its esters which are used, in the process of the present invention, as starting materials for the synthesis of precursors of 4'-hydroxybiphenyl4-carboxylic acid, an attempt has been made to prepare cyclohexanone-4-carboxylic acid methyl or ethyl ester by the hydrogenation of methyl or ethyl 4-hydroxybenzoate (see U.S. Pat. No. 4,537,704).

However, all of the prior art processes for the preparation of 4'-hydroxybiphenyl-4-carboxylic acid require expensive raw materials. Even in the process (a) using relatively cheap p-phenylphenol as the starting material, many steps are required and the raw materials used in each step are expensive. Moreover, this process also involves many problems from the viewpoint of waste disposal. Accordingly, the resulting 4'-hydroxybiphenyl-4-carboxylic acid necessarily becomes quite expensive. Thus, it may safely be said that no industrial process for the preparation of 4'-hydroxybiphenyl-4-carboxylic acid has not been proposed as yet.

SUMMARY OF THE INVENTION

It is an object of the present invention to provide a novel process for the preparation of 4'-hydroxybiphenyl-4-carboxylic acid by a new reaction route.

It is another object of the present invention to provide a process for the preparation of 4'-hydroxybiphenyl-4-carboxylic acid by using, as the starting material, a cyclohexanone-4-carboxylic acid compound which has been prepared by an improved process.

Other objects will become apparent from the following description.

According to the present invention, there is provided a process for the preparation of 4'-hydroxybiphenyl-4-carboxylic acid which comprises reacting a cyclohexanone-4-carboxylic acid compound of the formula

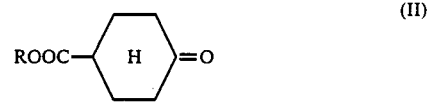

where R is a hydrogen atom or a lower alkyl group, with phenol in the presence of an acid catalyst to form a 4,4-bis(4-hydroxyphenyl)cyclohexanecarboxylic acid compound of the formula

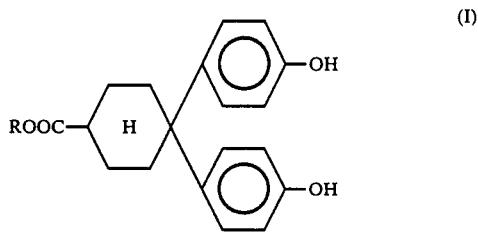

where R is as defined for formula (II); and then subjecting the 4,4-bis(4-hydroxyphenyl)cyclohexanecarboxylic acid compound to decomposition and dehydrogenation reactions in the presence of a base and a dehydrogenation catalyst.

The compounds within the scope of formula (I) are novel compounds as disclosed in copending Japanese patent application No. 8405/1986, filed Mar. 18, 1986 and assigned to the assignee hereof.

The compounds within the scope of formula (II) can be advantageously prepared by a process as disclosed in copending Japanese patent application No. 193986/1986, filed Aug. 21, 1986 and assigned to the assignee hereof. According to this process, the compounds of formula (II) are prepared by catalytically hydrogenating a 4-hydroxybenzoic acid compound of the formula

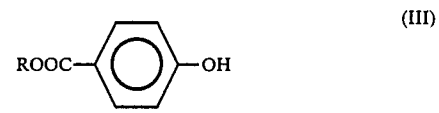

where R is as defined for formula (II), in a secondary alcohol or tertiary alcohol solvent capable of minimizing the formation of the over-hydrogenated product, or the corresponding cyclohexanol-4-carboxylic acid compound, which would otherwise be formed in an amount of 30% or more (see U.S. Pat. No. 4,537,704). The cyclohexanone-4-carboxylic acid compound thus obtained, which contains a small amount of the corresponding cyclohexanol4-carboxylic acid compound, can be directly used for the preparation of the compound of formula (I).

DETAILED DESCRIPTION OF THE PREFERRED EMBODIMENTS

In the practice of the present invention, the compound of formula (I) serving as a precursor of 4'-hydroxybiphenyl-4-carboxylic acid can be obtained by reacting a cyclohexanone-4-carboxylic acid compound of formula (II) with phenol in the presence of an acid catalyst.

Of course, it is preferable that the compound of formula (II) used for this reaction is in highly purified form. However, the compounds of formula (II) are so difficult to purify that a considerable loss thereof may be caused during the separation procedure.

Usually, a compound of formula (II) can be obtained by catalytically hydrogenating the corresponding 4-hydroxybenzoic acid compound with hydrogen in the presence of a reduction catalyst. During this reaction, the over-hydrogenated product (i.e., the corresponding cyclohexanol-4-carboxylic acid compound) is formed as a by-product in an amount of 30% or more, as described in the aforementioned U.S. Pat. No. 4,537,704.

After completion of the catalytic hydrogenation, therefore, it is necessary to separate such a large amount of the cyclohexanol-4-carboxylic acid compound from the reaction mixture. If the reaction mixture is heated to separate the cyclohexanol-4-carboxylic acid compound by distillation, this compound is easily converted into its lactone derivative with elimination of water or an alcohol.

Especially where the compound of formula (III) used as the starting material is a 4-hydroxybenzoic acid ester, the corresponding compound of formula (II) is obtained in high yield as a result of hydrogenation. However, the corresponding cyclohexanol-4-carboxylic acid ester (e.g., cyclohexanol-4-carboxylic acid methyl ester) is also formed as a by-product. Upon exposure to heat, this cyclohexanol-4-carboxylic acid methyl ester is easily converted into 2-oxabicyclo[2,2,2]-octan-3-one with elimination of methanol. Since this lactone derivative has a boiling point slightly different from that of cyclohexanone-4-carboxylic acid methyl ester, their separation by distillation requires a very large number of theoretical plates and a very high reflux ratio. Moreover, a considerable loss of cyclohexanone-4-carboxylic acid methyl ester is caused during the separation.

In the hydrogenation of a compound of formula (III), therefore, it is necessary to minimize the formation of a cyclohexanol-4-carboxylic acid compound. In the practice of the present invention, this can be accomplished by carrying out the hydrogenation in a secondary alcohol or tertiary alcohol solvent. In this manner, it becomes possible to obtain the desired cyclohexanone-4-carboxylic acid compound rapidly in high yield while minimizing the formation of a cyclohexanol-4-carboxylic acid compound and other by-products.

In the process of the present invention, the condensation reaction of the cyclohexanone-4-carboxylic acid compound with phenol may be carried out in the liquid phase at a relatively low temperature of 100° C. or below and usually 40°-70° C. Under such conditions, the presence of a small amount of the over-hydrogenated product (i.e., the cyclohexanol-4-carboxylic acid compound) formed as a by-product neither affects the reaction rate nor brings about the formation of its lactone derivative.

Accordingly, the reaction mixture resulting from the catalytic hydrogenation step can be directly used for the condensation reaction with phenol. Since the precursor of formula (I) resulting from the condensation reaction is formed as a solid precipitate, the overhydrogenated product (i.e., the cyclohexanol-4-carboxylic acid compound) present in the reaction mixture can be easily separated according to a solid-liquid separation technique. Thus, in a preferred embodiment of the present invention, there is provided an industrially advantageous process which comprises preparing a compound of formula (II) in a secondary alcohol or tertiary alcohol solvent; using the resulting reaction mixture, containing the compound of formula (II), directly for the reaction with phenol to form a precursor of formula (I); and then converting the precursor into the desired product, or 4'-hydroxybiphenyl-4-carboxylic acid.

In the practice of the present invention, a secondary alcohol or tertiary alcohol solvent is used in the catalytic hydrogenation of a compound of formula (III). The solvent used for this purpose is selected from among such compounds as are liquids at the reaction temperature employed and do not undergo hydrogenation under the reaction conditions employed. Usable solvents include, for example, aliphatic secondary alcohols such as isopropyl alcohol, sec-butyl alcohol, sec-amyl alcohol, diethylcarbinol, methylisobutylcarbinol, 3-heptanol, methylamylcarbinol, etc.; alicyclic secondary alcohols such as cyclopentanol, cyclohexanol, cyclooctanol, 2-methylcyclohexanol, 3-methylcyclohexanol, 4-methylcyclohexanol, dimethylcyclohexanol, trimethylcyclohexanol, etc.; and tertiary alcohols such as tert-butyl alcohol, tert-amyl alcohol, 1-methylcyclohexanol, etc.

Among these solvents, isopropyl alcohol is most preferred in consideration of its effectiveness in inhibiting the formation of a cyclohexanoe-4-carboxylic acid compound, its low price, its ease of separation and recovery after completion of the reaction, and the like.

The solvent is usually used in an amount of 0.5 to 5 parts by weight, preferably 1 to 3 parts by weight, for each part by weight of the hydroxybenzoic acid compound of formula (III).

The 4-hydroxybenzoic acid esters of formula (III) which can be used in the catalytic hydrogenation include methyl 4-hydroxybenzoate, ethyl 4-hydroxybenzoate and propyl 4-hydroxybenzoate. Among them, methyl 4-hydroxybenzoate is the most preferred raw material.

The catalytic hydrogenation is usually carried out in the presence of a catalyst. Although any of conventional hydrogenation catalysts may be used for this purpose, platinum metal catalysts and rhenium catalysts are preferred. Among others, palladium-carbon catalyst is most preferred.

The catalyst is usually used in an amount of 0.0001 to 0.2 gram atom, preferably 0.0003 to 0.01 gram atom, of catalyst metal atoms for each mole of the 4-hydroxybenzoic acid compound of formula (III).

The catalytic hydrogenation is usually carried out at a reaction temperature of 80° to 200° C. and a hydrogen pressure of 1 to 50 kg/cm$^2$, preferably 2 to 30 kg/cm$^2$. It is not advisable to employ higher hydrogen pressures, because this causes an increased formation of by-products.

The crude cyclohexanone-4-carboxylic acid compound obtained from the hydrogenation step may be directly used in the next step. More specifically, after the solvent is distilled off from the reaction mixture, the resulting reaction mass may be used for the subsequent condensation reaction without further purification. Although this reaction mass contains some impurities consisting mainly of a cyclohexanol-4-carboxylic acid compound, the precursor, or 4,4-bis(4-hydroxyphenyl)cyclohexanecarboxylic acid compound, resulting from condensation reaction with phenol does not contain such impurities. Of course, the process of the present invention may be carried out by distilling off the solvent from the reaction mixture resulting from the hydrogenation step, isolating the desired cyclohexanone-4-carboxylic acid compound according to conventional procedures such as rectification and the like, and then using it for the subsequent condensation reaction with phenol.

In the practice of the present invention, the cyclohexanone-4-carboxylic acid compound of formula (II) is reacted with phenol in the presence of an acid catalyst to obtain a precursor of formula (I), or a 4,4-bis(4-hydroxyphenyl)cyclohexanecarboxylic acid compound. Where a cyclohexanone-4-carboxylic acid ester is used for this reaction, part of the resulting 4,4-bis(4-hydroxyphenyl)cyclohexanecarboxylic acid ester is hydrolyzed under the action of the acid catalyst to form 4,4-bis(4-hydroxyphenyl)cyclohexanecarboxylic acid.

The acid catalysts which can be used for the condensation reaction of the compound of formula (II) with phenol include, for example, hydrogen chloride gas, hydrochloric acid, sulfuric acid, phosphoric acid, toluenesulfonic acid, $BF_3$, $ZnCl_2$, $AlCl_3$, $SnCl_4$, cation exchange resins having movable acid groups, and the like. The acid catalyst is used in an amount of 0.1 to 30 parts by weight per 100 parts by weight of the cyclohexanone-4-carboxylic acid compound of formula (II).

Moreover, the reaction rate can further be enhanced by the addition of a co-catalyst. Active cocatalysts include alkyl mercaptans such as methyl mercaptan, ethyl mercaptan, n-propyl mercaptan, isopropyl mercaptan, n-butyl mercaptan, isobutyl mercaptan, tert-butyl mercaptan, etc., as well as high-molecular-weight alkyl mercaptans.

It is also possible to use other sulfur compounds such as hydrogen sulfide, thiophenol, thioalcohols, thio acids, polymeric thioacetone, dialkyl sulfides, etc., as well as analogous selenium compounds.

The condensation reaction may be carried out in a solvent which exerts no adverse influence on the reaction, and usable solvents include aromatic hydrocarbons, chlorinated aliphatic hydrocarbons, glacial acetic acid, and the like. However, in order to enhance the yield of the product and minimize the occurrence of side reactions, it is desirable to use an excess of phenol as the solvent. The amount of phenol used is suitably in the range of 2 to 10 parts by weight for each part by weight of the cyclohexanone-4-carboxylic acid compound.

The condensation reaction is carried out at a reaction temperature of 30° to 100° C. and preferably 40° to 70° C. If the reaction temperature is too high, the formation of by-products will undesirably increase and, therefore, cause a reduction in the yield of the product.

The precursor so formed, or the 4,4-bis(4hydroxyphenyl)cyclohexanecarboxylic acid ester, which may usually contain the free acid formed as a by-product, can be isolated by pouring the reaction mixture into a solvent (such as benzene or the like) in which those compounds are hardly soluble, and then cooling the resulting mixture to crystallize them. The precursor thus obtained is then used for the subsequent decomposition and dehydrogenation reactions. Where the reaction mass resulting from the catalytic hydrogenation is directly used for the condensation reaction, the cyclohexanol-4-carboxylic acid compound present therein as a by product does not react with phenol and, therefore, remains in the liquid phase during the aforesaid isolation procedure. The phenol used in excess can be recovered and reused by neutralizing the mother liquor and filtering off the crystallized salts, or by distilling the mother liquor under reduced pressure.

Where a cyclohexanone-4-carboxylic acid ester of formula (II) is used for the condensation reaction, the amount of 4,4-bis(4-hydroxyphenyl)cyclohexanecarboxylic acid formed as a by-product by hydrolysis of the condensation product is about 10 to 30% by weight under ordinary conditions. In this case, the resulting mixture of the precursor and the by-product may be used for the subsequent decomposition and dehydrogenation reactions without separating the by-product therefrom. Of course, it is not precluded to separate the by-product from the precursor prior to use.

Although the decomposition and dehydrogenation reactions of the present invention may be effected in separate steps, it is more efficient to carry out these reactions in a single step.

The decomposition reaction is carried out in the presence of a basic catalyst. Efficient basic catalysts for the decomposition reaction include alkali metal hydroxides such as sodium hydroxide, potassium hydroxide, lithium hydroxide, etc.; alkaline earth metal hydroxides such as magnesium hydroxide, barium hydroxide, etc.; carbonates; acetates; phenoxides; and salts of organic weak acids.

Among these catalysts, strongly basic catalysts such as sodium hydroxide and the like are preferred. The catalyst is usually used in an amount of 2 to 40% by weight, preferably 5 to 20% by weight, based on the 4,4-bis(4-hydroxyphenyl)cyclohexanecarbocylic acid compound of formula (I).

In the decomposition and dehydrogenation step, such a basic catalyst easily hydrolyze the ester group in the compound of formula (I) to convert it into the free carboxylic acid and thereby produce the desired product in high yield.

The dehydrogenation reaction is usually carried out in the presence of a catalyst. Although any of conventional dehydrogenation catalysts can be used for this purpose, specific examples thereof include nickel catalysts such as Raney nickel, reduced nickel, nickel-carrier catalysts comprising nickel supported on diatomaceous earth, alumina, pumice, silica gel, acid clay or other carrier, etc.; cobalt catalysts such as Raney cobalt, reduced cobalt, cobalt-carrier catalysts, etc.; copper catalysts such as Raney copper, reduced copper, copper-carrier catalysts, etc.; palladium catalysts such as palladium black, palladium oxide, colloidal palladium, palladium-carbon, palladium-barium sulfate, palladium-magnesium oxide, palladium-calcium oxide, palladium-alumina, etc.; platinum catalysts such as platinum black, colloidal platinum, platinum oxide, platinum sulfide, paltinum-carrier catalysts (e.g., platinum-carbon), etc.; rhodium catalysts such as colloidal rhodium, rhodium-carbon, rhodium oxide, etc.; other platinum metal catalysts such as ruthenium catalysts; rhenium catalysts such as dirhenium heptoxide, rhenium-carbon, etc.; copper chromium oxide catalyst; molybdenum oxide catalyst; vanadium oxide catalyst; tungsten oxide catalyst; silver catalysts; and the like.

Among these catalysts, platinum metal catalysts such as palladium catalysts are preferred. The dehydrogenation catalyst is usually used in an amount of 0.001 to 0.2 gram atom, preferably 0.004 to 0.1 gram atom, of catalyst metal atoms for each mole of the precursor of formula (I), or the 4,4-bis(4-hydroxyphenyl)cyclohexanecarboxylic acid compound.

Although the dehydrogenation reaction may be carried out without using any hydrogen acceptor, the co-presence of a hydrogen acceptor can enhance the yield.

Although any hydrogen acceptor may be used, several types of compounds are useful for this purpose. They include, for example, organic compounds containing ethylenic unsaturation, such as ethylene, propylene, etc.; organic compounds containing acetylenic unsaturation, such as acetylene, methylacetylene, etc.; organic compounds containing an azo group or groups, such as azobenzene, etc.; nitro or carbonyl compounds; phenolic compounds; and the like.

Among these hydrogen acceptors, organic compounds containing conjugated double bonds, such as styrene compounds (e.g., α-methylstyrene), nitrobenzene, maleic anhydride, methylacetylene, crotonic acid, phenol, etc., are preferred. Moreover, it is recommendable to select hydrogen acceptors which not only have high activity, but also yield useful products as a result of hydrogenation (such as cumene for α-methylstyrene, cyclohexanone for phenol, and the like).

The decomposition and dehydrogenation reactions are usually carried out at a reaction temperature of 100° to 400° C., preferably 180° to 300° C. If the reaction temperature is lower, the reaction rate will be unduly low, while if it is higher, undesirable side reactions may take place.

The reactions may be carried out in the gaseous phase, but high temperatures of 300° C. or above are required in such a case because of the high melting points of the raw materials and products. Accordingly, it is preferable from the viewpoints of yield, operability, energy cost and the like to carry out the reactions in the liquid phase. In this case, the use of a solvent is recommendable. Specific examples of useful solvents include water; ethers such as ethylene glycol monomethyl ether, ethylene glycol dimethyl ether, diethylene glycol monomethyl ether, tetrahydrofuran, dioxane, dipropyl ether, diphenyl ether, etc.; alcohols such as ethanol, isopropanol, ethylene glycol, diethylene glycol, triethylene glycol, propylene glycol, etc.; nitriles such as acetonitrile, propionitrile, benzonitrile, etc.; aromatic hydrocarbons such as benzene, toluene, xylene, mesitylene, ethylbenzene, cumene, etc.; and the like. It is also possible to use the above-defined hydrogen acceptor as a solvent.

The 4-hydroxybiphenyl-4-carboxylic acid formed in the above described manner can be obtained in highly purified form and in high yield by removing the solvent from the resulting reaction mixture and then isolating the desired product according to conventional procedures such as crystallization and the like.

The present invention is more specifically explained with reference to the following examples.

EXAMPLE 1

Into a 300-ml stainless steel autoclave were charged 45.6 g (0.30 mole) of methyl 4-hydroxybenzoate, 0.23 g of 5% palladium-carbon catalyst, and 100 ml of propyl alcohol. After the air within the autoclave was displaced with nitrogen gas, the reaction mixture was allowed to absorb 0.60 mole of hydrogen at a temperature of 180° C. and a gauge pressure of 20 kg/cm². After the reaction mixture was cooled and filtered to remove the catalyst therefrom, the solvent was distilled off to obtain 47.0 g of a reaction mass.

All of the aforesaid reaction mass, 110.0 g of phenol, and 10 ml of 36% hydrochloric acid were charged into a 300-ml reaction flask, and reacted at 60° C. for 5 hours. After completion of the reaction, the reaction mixture was poured into 300 ml of benzene, followed by stirring at room temperature for 3 hours. The precipitate so formed was collected by filtration, washed and then dried to obtain 65.0 g of white crystals.

Next, all of the aforesaid white crystals, 8.2 g of sodium hydroxide, 1.2 g of 5% palladium-carbon catalyst, 66.0 g of α-methylstyrene, and 300 ml of water were charged into a 500-ml stainless steel autoclave. After the air within the autoclave was displaced with nitrogen gas, the reaction mixture was heated at 250° C. for 4 hours. After completion of the reaction, the reaction mixture was cooled. Since some crystals separated out, 100.0 g of a 20% aqueous solution of sodium hydroxide was added to the reaction mixture so as to dissolve the crystals. Thereafter, the reaction mixture was filtered to remove the catalyst therefrom. After the filtrate was extracted with 300 ml of benzene to recover α-methylstyrene and cumene, diluted hydroxhloric acid was added thereto so as to precipitate 4'-hydroxybiphenyl-4-carboxylic acid. The crystals so formed were collected by filtration, washed with water, and then dried to obtain 42.4 g of 4'-hydroxybiphenyl-4-carboxylic acid.

Liquid-chromatographic analysis revealed that this product had a purity of 91.2%, and its yield based on the amount of methyl p-hydroxybenzoate used was 60.2%.

EXAMPLE 2

Into a 300-ml stainless steel autoclave were charged 45.6 g (0.30 mole) of methyl 4-hydroxybenzoate, 0.23 g of 5% palladium-carbon catalyst, and 100 ml of propyl alcohol. After the air within the autoclave was displaced with nitrogen gas, the reaction mixture was allowed to absorb 0.60 mole of hydrogen at a temperature of 180° C. and a gauge pressure of 20 kg/cm². After cooling, the catalyst was filtered off to obtain a reaction mass.

The reaction mass thus obtained was evaporated to separate isopropyl alcohol therefrom. Then, using a distillation column packed with Dickson's packing material and having a number of theoretical plates of 20, the residue was distilled at a reflux ratio of 2–10 to obtain 33.2 g of cyclohexanone-4-carboxylic acid methyl ester as the distillate at 144° C./30 mmHg. This product has a purity of 96%, and the greater part of the impurities comprised 2-oxabicyclo[2,2,2]octan-3-one

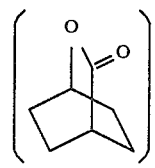

Next, 62.5 g (0.40 mole) of the cyclohexanone-4-carboxylic acid methyl ester prepared and purified in the above-described manner, 188.2 g (2.0 moles) of phenol, and 20 ml of 36% hydrochloric acid were charged into a 300-ml reaction flask, and reacted by stirring at 40°–45° C. for 5 hours. After completion of the reaction, the reaction mixture was poured into 500 ml of benzene, followed by stirring at 20° C. for 1 hour. The precipitate so formed was collected by filtration and then dried to obtain 103.7 g of white crystals. Liquid-chromatographic analysis revealed that this product comprised 82.2% of 4,4-bis(4-hydroxyphenyl)cyclohexanecarboxylic acid methyl ester and 17.7% of 4,4-bis(4-hydroxyphenyl)cyclohexanecarboxylic acid.

Next, 20.0 g of the aforesaid white crystals, 2.7 g of sodium hydroxide, 21.9 g of α-methylstyrene, 100 g of water, and 0.4 g of 5% palladium-carbon catalyst were charged into a 300-ml stainless steel autoclave. After the air within the autoclave was displaced with nitrogen gas, the reaction mixture was heated at 250° C. for 4 hours. After completion of the reaction, the reaction mixture was cooled. Since some crystals separated out, 30.0 g of a 20% aqueous solution of sodium hydroxide was added to the reaction mixture so as to dissolve the crystals. Thereafter, the reaction mixture was filtered to remove the catalyst therefrom. After the filtrate was extracted with 100 ml of benzene to recover α-methylstyrene and cumene, diluted hydroxhloric acid was added thereto so as to precipitate 4'-hydroxy-biphenyl-4-carboxylic acid. The crystals so formed were collected by filtration, washed with water, and then dried to obtain 13.0 g of 4'-hydroxybiphenyl-4-carboxylic acid having a melting point of 297° C. Liquid-chromatographic analysis revealed that this product had a purity of 99%, and its total yield based on the amount of cyclohexanone-4-carboxylic acid methyl ester used was 78%.

EXAMPLE 3

In the same manner as described in Example 2, 68.1 g (0.40 mole) of cyclohexanone-4-carboxylic acid ethyl ester was condensed with phenol and then worked up to obtain 109.6 g of a mixture comprising 82.4% of 4,4-bis(4-hydroxyphenyl)cyclohexanecarboxylic acid ethyl ester and 17.6% of 4,4-bis(4-hydroxyphenyl)cyclohexanecarboxylic acid. Thereafter, in the same manner as described in Example 2, 20.0 g of the aforesaid mixture was subjected to cleavage and dehydrogenation reactions and then worked up to obtain 12.5 g of 4'-hydroxybiphenyl-4-carboxylic acid having a purity of 99%. Its total yield based on the amount of cyclohexanone-4-carboxylic acid ethyl ester used was 79%.

EXAMPLE 4

Into a stainless steel autoclave were charged 41.4 g (0.30 mole) of methyl 4-hydroxybenzoate, 2.1 g of 5% palladium-carbon catalyst, and 100 ml of isopropyl alcohol. After the air within the autoclave was displaced with nitrogen gas, the reaction mixture was allowed to absorb 0.60 mole of hydrogen at a temperature of 120° C. and a gauge pressure of 20 kg/cm². After the reaction mixture was cooled and filtered to remove the catalyst therefrom, the solvent was distilled off to obtain 42.8 g of white crystals. Gas-chromatographic analysis revealed that this product had a cyclohexanone-4-carboxylic acid content of 40.2%, and its yield was 40.3%.

From the reaction mass thus obtained, cyclohexanone-4-carboxylic acid was isolated in purified form and then subjected to a condensation reaction in the same manner as described in Example 1.

Next, 18.7 g (0.060 mole) of the 4,4-bis(4-hydroxyphenyl)cyclohexanecarboxylic acid thus obtained, 2.9 g (0.072 mole) of sodium hydroxide, 100.0 g of phenol, and 0.4 g of 5% palladium-carbon catalyst were charged into a 300-ml stainless steel autoclave. After the air within the autoclave was displaced with nitrogen gas, the reaction mixture was heated at 200° C. for 6 hours. After completion of the reaction, the reaction mixture was filtered to separate unreacted phenol therefrom. The filter cake was dissolved in 50 g of a 20% aqueous solution of sodium hydroxide, and the resulting solution was filtered again to recover the catalyst. In order to precipitate the desired product, the filtrate was brought to pH 1 by the addition of diluted hydrochloric acid. The crystals so formed were collected by filtration, washed with water, and then dried to obtain 11.7 g of 4'-hydroxybiphenyl-4-carboxylic acid in the form of white crystals. Liquid-chromatographic analysis revealed that this product had a purity of 93%, and the greater part of the impurities comprised 4-(4'-hydroxyphenyl)cyclohexanecarboxylic acid. On the basis of the amount of 4,4-bis(4-hydroxyphenyl)cyclohexanecarboxylic acid used, the yield of 4'-hydroxybiphenyl-4-carboxylic acid as corrected for its purity was 85%.

EXAMPLE 5

Into a 300-ml stainless steel autoclave were charged 18.7 g (0.060 mole) of 4,4-bis(4-hydroxyphenyl)cyclohexanecarboxylic acid, 2.9 g (0.072 mole) of sodium hydroxide, 100.0 g of phenol, and 0.4 g of 5% palladium-carbon catalyst. After the air within the autoclave was displaced with nitrogen gas, the reaction mixture was heated at 200° C. for 6 hours. After completion of the reaction, the reaction mixture was filtered to separate unreacted phenol therefrom. The filter cake was dissolved in 50 g of a 20% aqueous solution of sodium hydroxide, and the resulting solution was filtered again to recover the catalyst. In order to precipitate the desired product, the filtrate was brought to pH 1 by the addition of diluted hydrochloric acid. The crystals so formed were collected by filtration, washed with water, and then dried to obtain 11.7 g of 4'-hydroxybiphenyl-4-carboxylic acid in the form of white crystals. Liquid-chromatographic analysis revealed that this product had a purity of 93%, and the greater part of the impurities comprised 4-(4'-hydroxyphenyl)cyclohexanecarboxylic acid. The yield of 4'-hydroxy-biphenyl-4-carboxylic acid as corrected for its purity was 85%.

EXAMPLE 6

Into a 300-ml stainless steel autoclave were charged 19.6 g (0.060 mole) of 4,4-bis(4-hydroxyphenyl)cyclohexanecarboxylic acid methyl ester, 2.9 g (0.072 mole) of sodium hydroxide, 21.3 g (0.18 mole) of α-methylstyrene, 0.4 g of 5% palladium-carbon catalyst, and 100 g of cumene. The reaction was conducted in the same manner as described in Example 1. The resulting reaction mixture was worked up in the same manner as described in Example 1 to obtain 11.6 g 4'-hydroxybiphenyl-4-carboxylic acid in the form of white crystals. This product contained practically no impurities, and its yield as corrected for its purity was 90%.

What is claimed is:

1. A process for the preparation of 4'-hydroxybiphenyl-4-carboxylic acid which comprises reacting a cyclohexanone-4-carboxylic acid compound of the formula

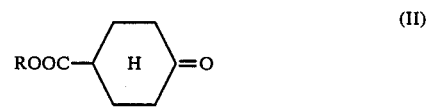

where R is a hydrogen atom or a lower alkyl group, with phenol in the presence of an acid catalyst to form a 4,4-bis(4-hydroxyphenyl)cyclohexanecarboxylic acid compound of the formula

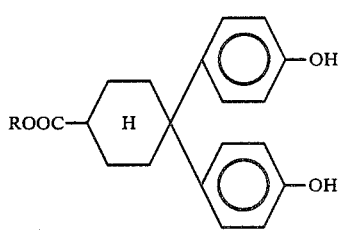
(I)

where R is as defined for formula (II); and then subjecting the 4,4-bis(4-hydroxyphenyl)cyclohexanecarboxylic acid compound to decomposition and dehydrogenation reactions in the presence of a base and a dehydrogenation catalyst.

2. A process as claimed in claim 1 wherein the dehydrogenation catalyst is a catalyst containing palladium or platinum.

3. A process as claimed in claim 1 wherein the decomposition and dehydrogenation reactions are carried out in the presence of a hydrogen acceptor in addition to the base and the dehydrogenation catalyst.

4. A process for the preparation of 4'-hydroxybiphenyl-4-carboxylic acid which comprises catalytically hydrogenating a 4-hydroxybenzoic acid compound of the formula

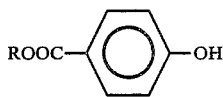
(III)

where R is a hydrogen atom or a lower alkyl group, in a secondary alcohol or tertiary alcohol solvent to obtain a cyclohexanone-4-carboxylic acid compound of the formula

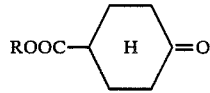
(II)

where R is as defined for formula (III); continuously reacting the cyclohexanone-4-carboxylic acid compound with phenol in the presence of an acid catalyst to form a 4,4-bis(4-hydroxyphenyl)cyclohexanecarboxylic acid compound of the formula

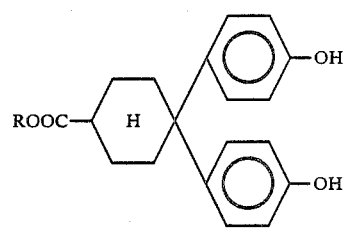
(I)

where R is as defined for formula (III); and then subjecting the 4,4-bis(4-hydroxyphenyl)cyclohexanecarboxylic acid compound to decomposition and dehydrogenation reactions in the presence of a base and a dehydrogenation catalyst.

5. A process as claimed in claim 4 wherein the dehydrogenation catalyst is a catalyst containing palladium or platinum.

6. A process as claimed in claim 4 wherein the decomposition and dehydrogenation reactions are carried out in the presence of a hydrogen acceptor in addition to the base and the dehydrogenation catalyst.

7. A process for the preparation of 4'-hydroxybiphenyl-4-carboxylic acid which comprises subjecting a 4,4-bis(4-hydroxyphenyl)cyclohexanecarboxylic acid compound of the formula

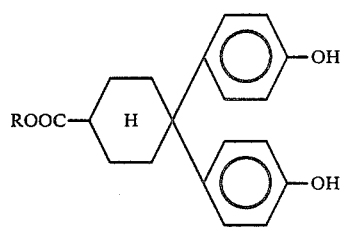
(I)

where R is a hydrogen atom or a lower alkyl group, to decomposition and dehydrogenation reactions in the presence of a base and a dehydrogenation catalyst.

8. A process as claimed in claim 7 wherein the dehydrogenation catalyst is a catalyst containing palladium or platinum.

9. A process as claimed in claim 7 wherein the decomposition and dehydrogenation reactions are carried out in the presence of a hydrogen acceptor in addition to the base and the dehydrogenation catalyst.

* * * * *

UNITED STATES PATENT AND TRADEMARK OFFICE
CERTIFICATE OF CORRECTION

PATENT NO. : 4,755,617

DATED : July 5, 1988

INVENTOR(S) : MIURA et al.

It is certified that error appears in the above-identified patent and that said Letters Patent is hereby corrected as shown below:

On the title page and column 1, line 3, title of invention should read

-- [54] PROCESS FOR THE PREPARATION OF 4'-HYDROXYBIPHENYL-4-CARBOXYLIC ACID --.

Signed and Sealed this

Seventeenth Day of January, 1989

Attest:

DONALD J. QUIGG

Attesting Officer

Commissioner of Patents and Trademarks